(12) United States Patent
Meridew

(10) Patent No.: US 9,572,686 B2
(45) Date of Patent: Feb. 21, 2017

(54) CARTILAGE REPAIR SYSTEM WITH FLEXIBLE TREPHINE

(71) Applicant: Biomet Manufacturing, LLC, Warsaw, IN (US)

(72) Inventor: Jason D. Meridew, Warsaw, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 0 days.

(21) Appl. No.: 14/456,334

(22) Filed: Aug. 11, 2014

(65) Prior Publication Data

US 2014/0350585 A1    Nov. 27, 2014

Related U.S. Application Data

(62) Division of application No. 12/862,378, filed on Aug. 24, 2010, now Pat. No. 8,801,716.

(51) Int. Cl.
*A61F 2/46* (2006.01)
*A61B 17/16* (2006.01)
*A61B 17/17* (2006.01)

(52) U.S. Cl.
CPC ......... *A61F 2/4618* (2013.01); *A61B 17/1635* (2013.01); *A61B 17/1637* (2013.01);
(Continued)

(58) Field of Classification Search
CPC ............ A61F 2/4618; A61F 2002/4649; A61F 2002/4627; A61F 2002/4687; A61B 17/1631; A61B 17/1637; A61B 17/1764; A61B 17/1635; A61B 17/1664
(Continued)

(56) References Cited

U.S. PATENT DOCUMENTS 4,696,308 A    9/1987 Meller et al.
4,751,922 A    6/1988 DiPietropolo
(Continued)

FOREIGN PATENT DOCUMENTS

WO    WO-2008100484 A1    8/2008

OTHER PUBLICATIONS

"U.S. Appl. No. 12/862,378, Examiner Interview Summary mailed Feb. 24, 2014", 3 pgs.
(Continued)

*Primary Examiner* — Todd E Manahan
*Assistant Examiner* — Marcela I Shirsat
(74) *Attorney, Agent, or Firm* — Schwegman Lundberg & Woessner, P.A.

(57) ABSTRACT

A system for repairing cartilage includes a trephine having a passage extending along a longitudinal axis of the trephine. The trephine has a distal end and a proximal end. The distal end includes a cutting member operable to cut a cartilage plug from a donor site. The passage is operable to receive the cartilage plug. Also, the trephine is flexible to selectively move between a first position in which the longitudinal axis is substantially linear and a second position in which the longitudinal axis is nonlinear. Moreover, the system includes a guide tool that is removably coupled to the trephine. The guide tool is operable to selectively move the trephine between the first and second positions. In addition, the system includes an ejector tool that ejects the cartilage plug from the passage toward a defect site.

20 Claims, 3 Drawing Sheets

(52) U.S. Cl.
CPC ....... *A61B 17/1631* (2013.01); *A61B 17/1764* (2013.01); *A61F 2002/4627* (2013.01); *A61F 2002/4649* (2013.01); *A61F 2002/4687* (2013.01); *Y10T 408/895* (2015.01)

(58) Field of Classification Search
USPC ........................ 606/79–80, 86 R, 87–89, 96, 99,606/179–180, 909, 916; 408/204, 206, 209, 86; 144/208.8
See application file for complete search history.

(56) References Cited

U.S. PATENT DOCUMENTS

| | | | |
|---|---|---|---|
| 5,329,923 | A | 7/1994 | Lundquist |
| 5,387,218 | A | 2/1995 | Meswania |
| 5,395,188 | A * | 3/1995 | Bailey .................... B23B 47/28 408/127 |
| 5,488,761 | A | 2/1996 | Leone |
| 5,527,316 | A | 6/1996 | Stone et al. |
| 5,624,447 | A * | 4/1997 | Myers ............................ 606/96 |
| 5,782,835 | A | 7/1998 | Hart et al. |
| 5,840,013 | A | 11/1998 | Lee et al. |
| 5,921,987 | A * | 7/1999 | Stone ............................ 606/80 |
| 6,053,922 | A | 4/2000 | Krause et al. |
| 6,068,642 | A | 5/2000 | Johnson et al. |
| 6,447,518 | B1 | 9/2002 | Krause et al. |
| 6,764,452 | B1 | 7/2004 | Gillespie et al. |
| 6,835,198 | B2 | 12/2004 | Bonutti |
| 6,949,101 | B2 | 9/2005 | McCleary et al. |
| 8,801,716 | B2 | 8/2014 | Meridew |
| 2005/0137600 | A1 | 6/2005 | Jacobs et al. |
| 2006/0276247 | A1 | 12/2006 | Martinez |
| 2007/0043376 | A1 * | 2/2007 | Leatherbury et al. .......... 606/99 |
| 2007/0270711 | A1 | 11/2007 | Gil et al. |
| 2010/0094361 | A1 * | 4/2010 | Meneghini et al. ........ 606/86 R |

OTHER PUBLICATIONS

"U.S. Appl. No. 12/862,378, Final Office Action mailed Nov. 20, 2013", 15 pgs.

"U.S. Appl. No. 12/862,378, Non Final Office Action mailed May 7, 2013", 13 pgs.

"U.S. Appl. No. 12/862,378, Notice of Allowance mailed Mar. 31, 2014", 8 pgs.

"U.S. Appl. No. 12/862,378, Response filed Feb. 20, 2014 to Final Office Action mailed Nov. 20, 2013", 10 pgs.

"U.S. Appl. No. 12/862,378, Response filed Aug. 2, 2012 to Restriction Requirement mailed Jul. 3, 2012", 9 pgs.

"U.S. Appl. No. 12/862,378, Response filed Aug. 7, 2013 to Non Final Office Action mailed May 7, 2013", 13 pgs.

"U.S. Appl. No. 12/862,378, Restriction Requirement mailed Jul. 3, 2012", 7 pgs.

Kuroki, Hiroshi, et al., "Acoustic stiffness and change in plug cartilage over time after", Arthritis Research & Therapy. 6, [Online]. Retrieved from the Internet: <http://arthritis-research.com/content/6/6/R492>, (2004), R492-R504.

Lattermann, Christian, et al., "What's New in the Treatment of Focal Chondral Defects of the Knee?", Orthopedics. 29.10, [Online]. Retrieved from the Internet: <http://www.healio.com/orthopedics/journals/ORTHO/{6DEDFF36-21 B6-40BB-A5E8-1D5119B7CB93}/What146s-New-in-the-Treatment-of-Focai-Chondrai-Defects-of-the-Knee?full=1>, (2006), 13 pgs.

* cited by examiner

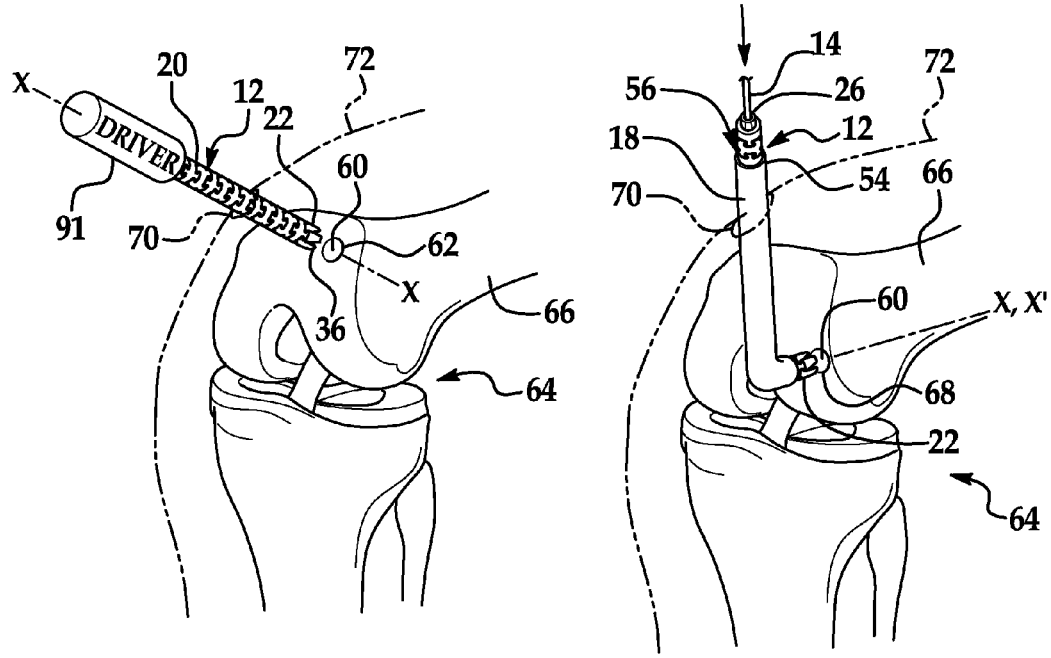
FIG. 5A  FIG. 5B
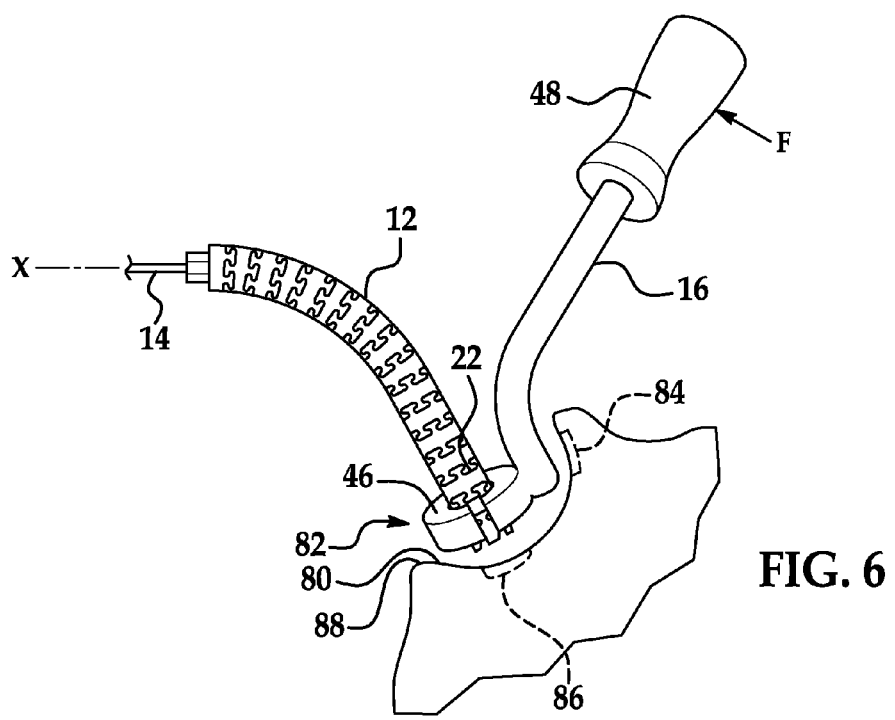
FIG. 6

CARTILAGE REPAIR SYSTEM WITH FLEXIBLE TREPHINE

CROSS-REFERENCE TO RELATED APPLICATIONS

This application is a divisional of U.S. application Ser. No. 12/862,378 filed on Aug. 24, 2010. The entire disclosure of the above application is incorporated herein by reference.

FIELD

The following relates to cartilage repair systems and methods and, more specifically, relates to a cartilage repair system with a flexible trephine and methods of use thereof.

BACKGROUND

The statements in this section merely provide background information related to the present disclosure and may not constitute prior art.

Various systems and procedures have been proposed for repairing damaged cartilage within a patient's body. For instance, healthy cartilage can be harvested from one area of the body (i.e., the donor site) and moved to another area of the body (i.e., the defect site) where cartilage is damaged. The harvested cartilage can be attached to the defect site, and the harvested cartilage can then grow on and repair the defect site.

In some cases, access to the donor and/or defect site can be limited. For instance, anatomical features may get in the way of certain instruments, thus limiting the ability of the surgeon to obtain cartilage from the donor site and/or place the harvested cartilage on the defect site. Also, the harvesting instruments may have limited access to the donor and/or defect site because these sites may have complex surface curvature. This limited access can complicate the harvesting procedure, for instance, necessitating multiple incisions in the patient, etc.

Thus, a system for repairing damaged cartilage is discussed in detail herein below. A method of using this system to repair damaged cartilage is also disclosed.

SUMMARY

A system for repairing cartilage is disclosed that includes a trephine having a passage extending along a longitudinal axis of the trephine. The trephine has a distal end and a proximal end. The distal end includes a cutting member operable to cut a cartilage plug from a donor site. The passage is operable to receive the cartilage plug. Also, the trephine is flexible to selectively move between a first position in which the longitudinal axis is substantially linear and a second position in which the longitudinal axis is nonlinear. Moreover, the system includes a guide tool that is removably coupled to the trephine. The guide tool is operable to selectively move the trephine between the first and second positions. In addition, the system includes an ejector tool that ejects the cartilage plug from the passage toward a defect site.

A method of repairing cartilage in a patient is also disclosed. The method includes operably coupling a guide tool to a trephine. The trephine has a longitudinal axis with a variable curvature. The method further includes guiding the trephine with the guide tool to adjust the curvature of the longitudinal axis of the trephine between a first curvature and a second curvature. Moreover, the method includes removing a cartilage plug from a donor site in the patient with the longitudinal axis of the trephine at the first curvature and attaching the cartilage plug to a defect site in the patient with the longitudinal axis of the trephine at the second curvature.

Still further, a method of repairing cartilage is disclosed that includes choosing between a first trephine and a second trephine that differ in size. Each of the first and second trephines have a respective longitudinal axis with a variable curvature. The method also includes forming an incision in a patient and inserting the chosen trephine through the incision into the patient. Furthermore, the method includes removing a cartilage plug from a donor site in a joint of the patient with a longitudinal axis of the chosen trephine being substantially straight and substantially normal to the donor site. Still further, the method includes operably and removably coupling a guide tool to the chosen trephine. Moreover, the method includes guiding the chosen trephine with the guide tool to adjust a curvature of the respective longitudinal axis of the chosen trephine to be non-linear to direct the respective longitudinal axis to be substantially normal to a defect site in the joint of the patient. Additionally, the method includes inserting a flexible ejector tool into the chosen trephine and advancing the ejector tool along the longitudinal axis to eject the cartilage plug toward the defect site and attaching the cartilage plug to the defect site.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 5A is a perspective view of a knee joint that is being repaired using the system of FIG. 1, wherein cartilage is being harvested from a donor site in the knee joint;

FIG. 5B is a perspective view of the knee joint of FIG. 5A, wherein harvested cartilage is being moved to a defect site in the knee joint using the system of FIG. 1; and FIG. 6 is a schematic view of a hip joint that is being repaired using the system of FIG. 1.

DETAILED DESCRIPTION

Figure 1:
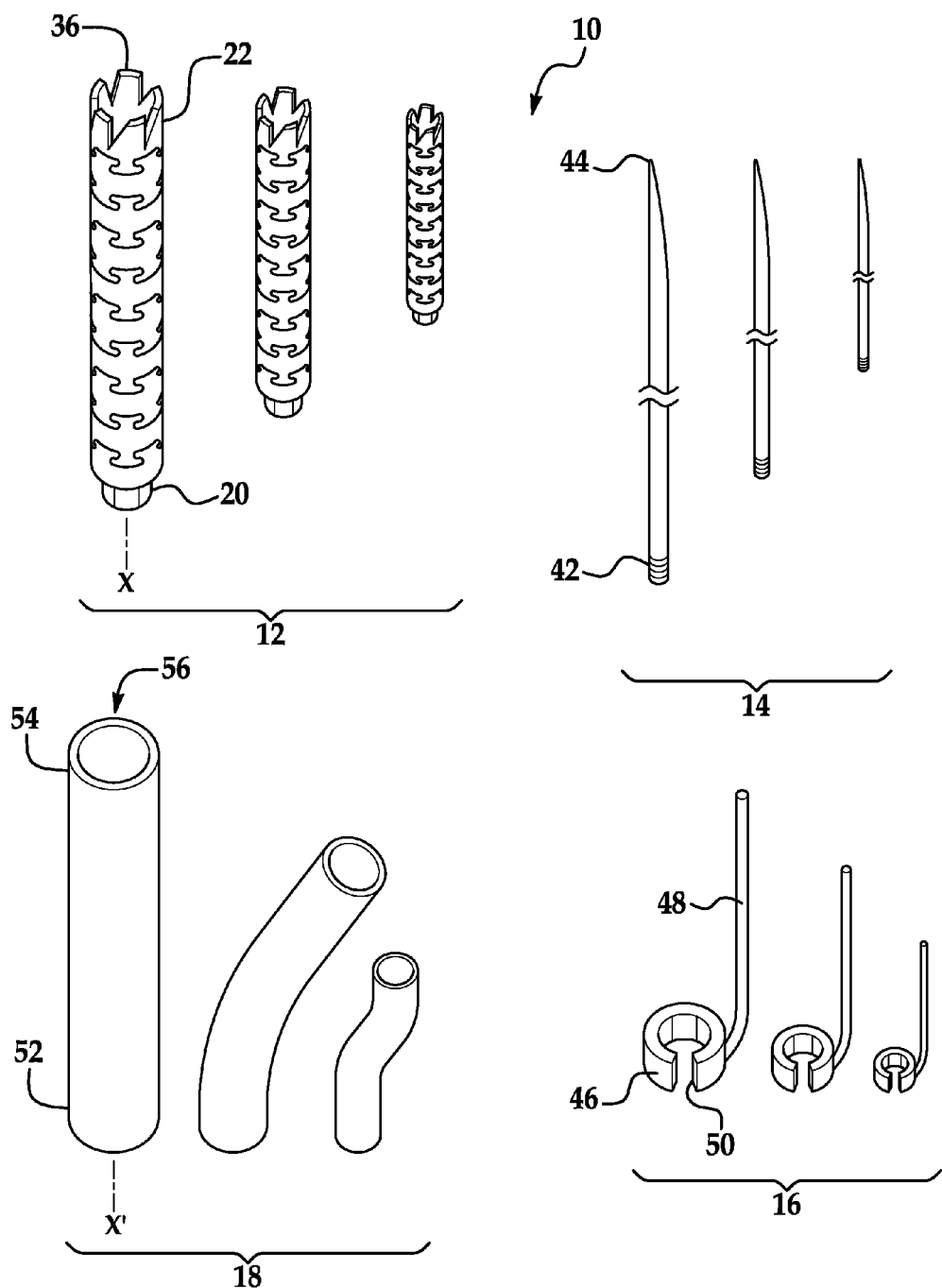
FIG. 1 is a schematic view of a system for repairing cartilage according to various exemplary embodiments of the present disclosure.

The following description is merely exemplary in nature and is not intended to limit the present disclosure, application, or uses. It should be understood that throughout the drawings, corresponding reference numerals indicate like or corresponding parts and features.

Referring initially to FIG. 1, a system 10 for repairing, harvesting, and placement of cartilage (e.g., a cartilage plug including both cartilage and attached bone tissue) is shown. The system 10 can generally include one or more trephines 12. Generally, the trephines 12 can each be elongate, hollow, and tubular. The trephines 12 can each include a proximal end 20 and a distal end 22. A cutting member 36 can be included on the distal end 22. Also, the trephines 12 can each be flexible such that a curvature of the longitudinal axis X of the trephine 12 can be selectively adjusted. More specifically, as will be discussed, the longitudinal axis X can be substantially linear (i.e., straight, can have substantially zero curvature, etc), and the trephine 12 can be selectively adjusted such that the axis X is non-linear (i.e., curved, can have positive curvature, etc.) The cutting member 36 can be rotationally driven to cut and harvest cartilage from an area of a patient, and the harvested cartilage can be received and retained within the distal end 22. The flexibility of the trephine 12 allows the trephine 12 to be routed more easily and conveniently toward desired locations in the patient's body as will be further discussed.

Furthermore, the system 10 can include one or more ejector tools 14. The ejector tools 14 can each be elongate and flexible. The ejector tools 14 can be received in respective trephines 12 and can be advanced along the axis X thereof to eject harvested cartilage from the trephines 12, as will be discussed in greater detail below.

Moreover, the system 10 can include one or more first guide tools 16. The first guide tools 16 can each include a respective coupling portion 46 and a handle 48 that extends therefrom. As will be discussed, the coupling portion 46 can be sized and shaped to removably engage and couple to a respective trephine 12, and the handle 48 can be used to guide and steer the respective trephine 12 by selectively moving and flexing (i.e., bending) the respective trephine 12. Accordingly, the first guide tools 16 can route and guide the respective trephine 12 and/or guide the distal end 22 of the respective trephine 12 toward a desired location in the patient as will be discussed in greater detail.

In addition, the system 10 can include one or more second guide or cannulated tools 18. Each second guide tool 18 can include an elongate, rigid, hollow (i.e., cannulated) tube with a proximal end 52 and a distal end 54. The second guide tools 18 can each have a respective longitudinal axis X'. In some embodiments, the axis X' can be straight and in other embodiments, the axis X' can be curved. In other embodiments, the second guide tools 18 can be non-resiliently bendable or malleable such that the curvature of the respective axis X' can be varied. Moreover, each second guide tool 18 can receive a respective trephine 12. Thus, if the second guide tool 18 has a positive curvature, then the respective trephine 12 can flex and bend along the curvature of the second guide tool 18 as the respective trephine advances along the second guide tool 18. Accordingly, the second guide tools 18 can route and guide the respective trephine 12 toward a desired location in the patient as will be discussed.

As shown in FIG. 1, the trephines 12 within the system 10 can differ from each other. For instance, the trephines 12 can differ in size (e.g., width, length, or any other suitable dimension). The trephines 12 can also differ in flexibility, in material, or in any other manner, such that the system 10 includes a wide variety of trephines 12. Likewise, the ejector tools 14 can differ in width, length, flexibility, material, or in any other suitable manner. Additionally, the first guide tools 16 can differ in size, material, etc. For instance, some of the first guide tools 16 can have similarly sized coupling portions 46 with differently sized handles 48 and vice versa. Furthermore, the second guide tools 18 can each vary in length, size, curvature, or in any other suitable manner. It will be appreciated that the system 10 can include any number and any variety of trephines 12, ejector tools 14, and first and second guide tools 16, 18.

Thus, the user can select between any of the trephines 12, the ejector tools 14, the first guide tools 16, and/or the second guide tools 18 for use. The selection can be based on the anatomical dimensions of a particular patient (e.g., the position, size, clearance, etc. of the cartilage donor and/or defect locations) or based on any other suitable basis. Thus, the system 10 can be very versatile.

Moreover, each trephine 12 can include a dedicated one of the ejector tools 14, the first guide tools 16 and/or the second guide tools 18. Thus, for example, when the user selects a trephine 12 for use, there can be an ejector tool 14, a first guide tool 16, and/or a second guide tool 18 that is clearly useable with the chosen trephine 12.

Figure 2:
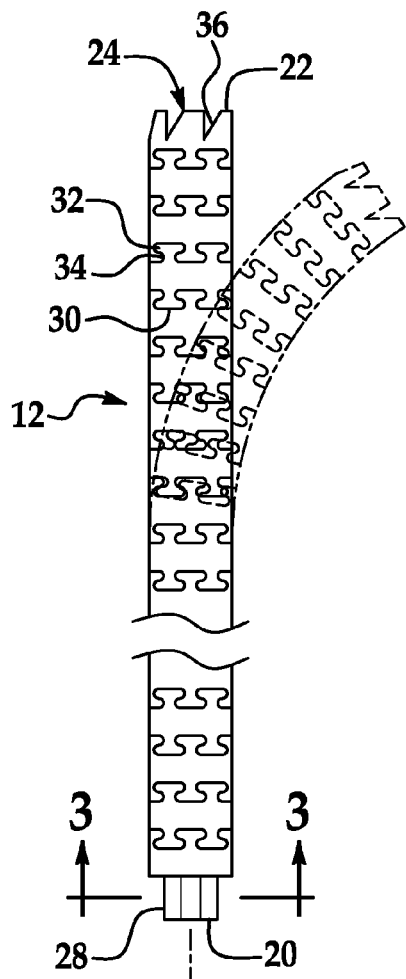
FIG. 2 is a front view of a flexible trephine of the system of FIG. 1 according to various exemplary embodiments of the present disclosure.
Figure 3:
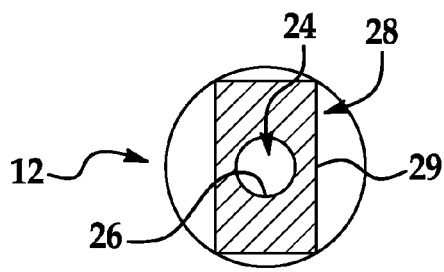
FIG. 3 is a section view of the trephine taken along the line 3-3 of FIG. 2.
Figure 4:
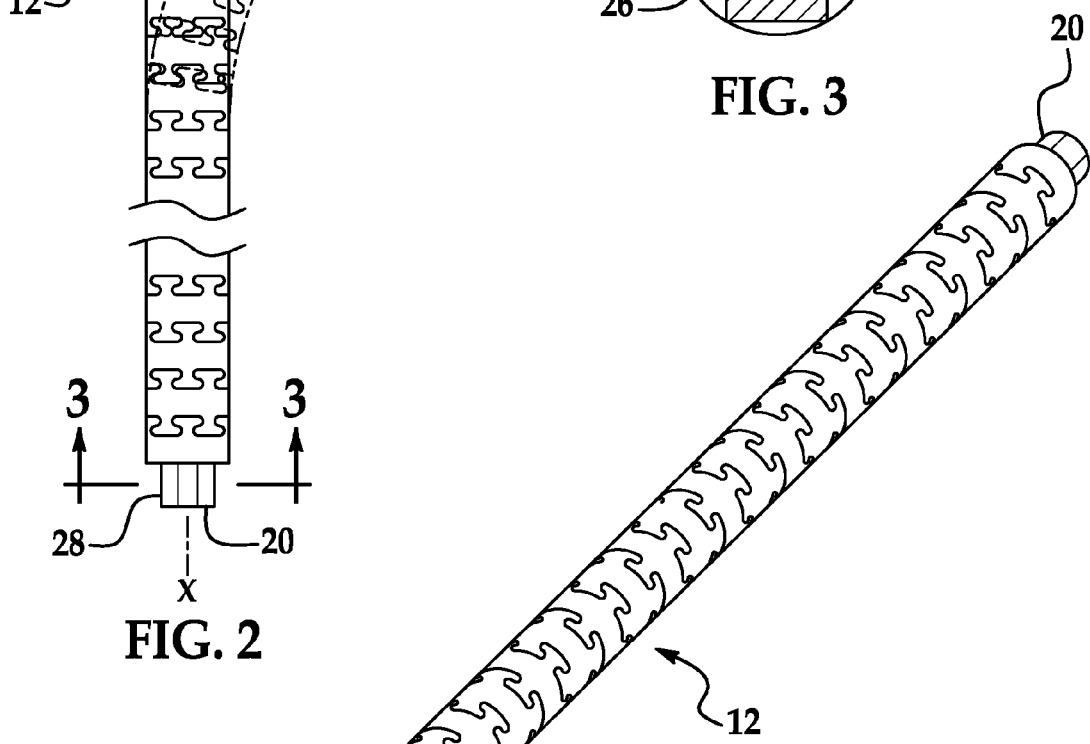
FIG. 4 is a perspective view of the flexible trephine of FIG. 2.

Referring now to FIGS. 2-4, a representative trephine 12 will be described in greater detail. As shown, the trephine 12 can be generally elongate with a proximal end 20 and a distal end 22, and with a longitudinal axis X (FIG. 2). The trephine 12 can also be hollow so as to define a passage 24 that extends along the entire longitudinal axis X. Furthermore, as shown in FIG. 3, the proximal end 20 of the trephine 12 can include an opening 26 (e.g., a through hole), which provides access to the passage 24 on the proximal end 20 of the trephine 12. Also, as shown in FIG. 2, the proximal end 20 can include a driver 28, which is operable to drive the trephine 12 in rotation about the longitudinal axis X. For instance, the driver 28 can be polygonal and/or can include one or more flat surfaces 29 (FIG. 3). The driver 28 can be rotationally driven by a powered tool or by manual power.

The trephine 12 can be made out of any suitable material. For instance, in some embodiments, the trephine 12 is made out of a rigid material, such as stainless steel.

Additionally, the cutting member 36 can include a plurality of sharpened edges 38 that are spaced equally about the longitudinal axis X and that are separated by a plurality of notches 40. As will be described, the cutting member 36 can be operable to cut and core a cartilage plug (i.e., cartilage and supporting bone tissue) away from a selected site in the patient when the trephine 12 drivingly rotates about the axis X. The cartilage plug can be received and retained within the passage 24 inside the trephine 12 such that the cartilage plug can be moved to a desired site within the patient.

Moreover, as stated above, the trephine 12 can be flexible. Accordingly, the trephine 12 can selectively bend and change the curvature of the longitudinal axis X. For instance, as shown in FIG. 2, the trephine 12 can selectively move between a first, axially straight or linear position (shown in solid lines in FIG. 2) and a second, axially curved or non-linear position (shown partially in phantom lines in FIG. 2). As will be described in greater detail below, the flexibility of the trephine 12 allows the trephine 12 to be routed, guided, or directed toward any suitable location. Accordingly, the flexibility of the trephine 12 allows for increased versatility. Also, the trephine 12 can be advantageously used in a minimally invasive manner (e.g., arthroscopically).

The trephine 12 can be flexible due to any suitable feature. For instance, as shown in FIGS. 2 and 4, the trephine 12 can include at least one slot 30. The slot 30 can be formed in any suitable fashion, such as laser cutting or wire EDM cutting. The slot 30 can continuously extend generally helically about the longitudinal axis X. Also, the slot 30 can define a plurality of projections 32 and a plurality of recesses 34. The projections 32 and recesses 34 can extend generally transverse to the longitudinal axis X. Also, the recesses 34 can receive respective projections 32, as shown in FIG. 4. Accordingly, the trephine 12 can flex about the slot 30 to allow the trephine 12 to bend along the longitudinal axis X. In some embodiments, the trephine 12 can flex between 0 and 90°. Also, the trephine 12 and the slot 30 can incorporate any suitable feature from U.S. Pat. No. 6,447,518, issued Sep. 10, 2002 to Krause et al., which is hereby incorporated by reference in its entirety.

Furthermore, torque can be transferred between the proximal and distal ends 20, 22 of the trephine because the projections 32 are received within respective recesses 34. Thus, as torque applied to the driver 28 can be transferred to the cutting member 36 on the distal end 22, regardless of whether the trephine 12 is axially straight or curved.

Referring back to FIG. 1, the ejector tools 14 will be described in greater detail. As shown, the ejector tools 14 can each be elongate and can include a proximal end 42 and a distal end 44. The distal end 44 can be tapered and pointed. Also, the ejector tools 14 can be flexible. Also, as will be discussed, the distal end 44 can be received within the opening 26 of the trephine 12 (see FIG. 5B) and the ejector tool 14 can extend longitudinally along the trephine 12. As will be discussed, the ejector tool 14 can extend from the proximal end 20 of the trephine 12 to the distal end 22 in order to push cartilage from the distal end 22 of the trephine 12.

Still referring to FIG. 1, the first guide tools 16 will be discussed in greater detail. As shown in FIG. 1, the first guide tools 16 can each include a coupling portion 46 and an elongate handle 48 that extends from the coupling portion 46. The coupling portion 46 can be substantially C-shaped so as to define an opening 50. Also, the coupling portion 46 can be resiliently flexible.

The coupling portion 46 can be operably and removably coupled to a respective trephine 12 in any suitable fashion. For instance, the trephine 12 can move through the opening 50 such that the coupling portion 46 resiliently expands, and as the trephine 12 is received within the coupling portion 46, the coupling portion 46 can resiliently snap fit and retain the trephine 12 therein due to friction (see FIG. 6). Also, when the coupling portion 46 is attached, a load applied to the handle 48 can transfer to the coupling portion 46 to thereby push or pull the trephine 12 and flexibly bend or guide the distal end 22 of the trephine 12 toward a desired location. Also, the coupling portion 46 can be removed from the trephine 12 by pulling the trephine 12 out of the coupling portion 46 through the opening 50. In some embodiments, the coupling portion 46 is only used to guide and bend the trephine 12 and is removed before the trephine 12 is driven in rotation; however, in other embodiments, the coupling portion 46 and the trephine 12 are slidingly engaged such that the trephine 12 can rotate within the coupling portion 46 to remove the cartilage plug, etc.

Additionally, as discussed above and as shown in FIG. 1, the second guide tools 18 can each be elongate so as to define a proximal end 52 and a distal end 54 as well as a respective axis X'. The second guide tools 18 can each be substantially rigid and hollow so as to define a passage 56 that extends between the proximal and distal ends 52, 54. The trephines 12 can be removably (e.g., slidably) received within the passage 56 of the second guide tools 18 and can be advanced from the proximal end 52 to the distal end 54 (see FIG. 5B).

It will be appreciated that the system 10 can include both the first guide tool 16 and the second guide tools 18. However, in other embodiments, the system 10 can include only either the first guide tools 16 or the second guide tools 18 without departing from the scope of the present disclosure. Also, it will be appreciated that the system 10 can include any suitable instrument (other than the first and second guide tools 16, 18) for guiding the trephines 12.

The method of using the system 10 will now be discussed in greater detail. Initially, the user can analyze the patient's anatomy, the location of the cartilage to be harvested, the location of the damaged cartilage, or any other necessary features. This analysis can be carried out using ultrasonic diagnostic tools, imaging tools (e.g., X-rays, MRI, etc.) or using any other suitable means. Using this information, the surgeon can select the corresponding trephine 12, ejector tool 14, and/or guide tool 16, 18 necessary to perform the procedure. For instance, the surgeon can select the proper size, shape, material, etc. necessary to perform the procedure for the specific patient.

Then, as shown in FIG. 5A, the system 10 can be used for removing or harvesting a cartilage plug 60 from a donor site 62 within a knee joint 64 of the patient. For instance, the donor site 62 can be located on a distal, anterior portion of a femur 66. Next, as shown in FIG. 5B, the system 10 can be used for attaching the cartilage plug 60 to a defect site 68 (i.e., the location of damaged cartilage) within the knee joint 64. For instance, the defect site 68 can be located on a posterior, condylar surface of the femur 66. As will be discussed, because of the flexibility of trephine 12, the same trephine 12 can be routed to both the donor site 62 as well as the defect site 68, despite differences in surface curvature and access to the donor and defect sites 62, 68.

Also, in some embodiments, the trephine 12 can be used to prepare the defect site 68. For instance, before the cartilage plug 60 is harvested from the donor site 62, the trephine 12 can be guided to the defect site 68 to remove a defective cartilage plug (i.e., defective cartilage and supporting bone tissue) and to form a hole, opening or recess at the defect site 68. Then, the trephine 12 can be removed from the patient, and the defective cartilage plug can be removed from the trephine 12. Next, the trephine 12 can be guided to the donor site 62 to harvest the cartilage plug 60, and then the trephine 12 can be guided to the defect site 68 for placement of the cartilage plug 60 in the prepared defect site 68. In still other embodiments, a tool other than the trephine 12 is used for preparing the defect site 68.

The procedure will now be discussed in greater detail. As shown in FIG. 5A, an incision 70 can be formed in the skin 72 of the patient (both shown in phantom). It will be appreciated that the method can be performed arthroscopically; thus, the incision 70 can be relatively small (e.g., slightly larger than the width of the trephine 12). In some embodiments, the knee joint 64 can be bent as shown in FIG. 5A, and the incision 70 can be made substantially directly over the donor site 62.

Assuming that the defect site 68 has already been prepared, the trephine 12 can be inserted into the patient through the incision 70 for harvesting the cartilage plug 60 from the donor site 62. In some embodiments, the trephine 12 can be inserted when the trephine 12 is axially straight, and the axis X of the trephine 12 can be directed substantially normal to the donor site 62. However, in other embodiments, the trephine 12 can be non-linear when advanced toward the donor site 62. Also, the distal end 22 of the trephine 12 can be advanced toward the donor site 62 using either the first or second guide tools 16, 18, or trephine 12 can be advanced independently, without the aid of the guide tools 16, 18.

Furthermore, the trephine 12 can be operably coupled at the proximal end 20 to a motorized device 91. More specifically, the motorized device 91 can include a chuck or other suitable coupling for operably coupling to the driver 28 of the trephine 12 such that the motorized device 91 can drivingly rotate the trephine 12 about the longitudinal axis X.

As the trephine 12 rotates over the donor site 62 and the trephine 12 is maintained in an axially straight position, the cutting member 36 can cut and core the cartilage plug 60 from the donor site 62, and the cartilage plug 60 can be received and retained within the distal end 22 of the trephine 12.

Next, as shown in FIG. 5B, the curvature of the trephine 12 can be adjusted such that the trephine 12 curves from the incision 70 toward the defect site 68. More specifically, the trephine 12 can be removed from the patient, and an appropriate second guide tool 18 can be inserted through the incision 70 and directed toward the defect site 68. Then, the trephine 12 can be inserted into the proximal end 52 of the second guide tool 18 and advanced along the passage 56 of the second guide tool 18 in order to guidingly bend the trephine 12 toward the defect site 68. In some embodiments, the second guide tool 18 can curve the trephine 12 toward the defect site 68 such that the axis X of the trephine 12 is directed substantially normal to the defect site 68.

Subsequently, as shown in FIG. 5B, the ejector tool 14 can be inserted into the opening 26 and advanced along the trephine 12 toward the cartilage plug 60 retained within the distal end 22 of the trephine 12. The ejector tool 14 can then be used to push the cartilage plug 60 out onto the prepared defect site 68. The mass of cartilage plug 60 can be pressed against the defect site 68 and retained on the defect site 68 through any suitable means, such as a press fit, frictional fit, or any other suitable means. Eventually, the mass of cartilage plug 60 can attach and grow on the defect site 68 to restore proper function of the knee joint.

Referring now to FIG. 6, another method of using the system 10 will be described. As shown, the system 10 can be used for harvesting and replacing cartilage in an acetabular cup 80 of a hip joint 82. The method of use is substantially similar to the method of use described above with respect to FIGS. 5A and 5B. However, as shown in FIG. 6, the first guide tool 16 can be used to adjust the curvature of the trephine 12 instead of the second guide tool 18.

More specifically, after the trephine 12 has harvested and collected the cartilage plug from the donor site 84, the coupling portion 46 of the guide tools 16 can be operably coupled to the distal end 22 of the trephine 12 as discussed above. Then, a load F can be applied to the handle 48 (which is extending out of the patient) in order to curve and route the trephine 12 toward the defect site 86.

It will be appreciated that the longitudinal axis X of the trephine 12 can be directed substantially normal to both the donor site 84 and the defect site 86 by adjusting the curvature of the trephine 12, as described above. Furthermore, it will be appreciated that the flexibility of the trephine 12 allows the trephine 12 to be maneuvered within the acetabular cup 80 in a convenient manner. For instance, the trephine 12 can be curved around the rim 88 of the acetabular cup 80 such that the trephine 12 is unlikely to abut against the rim 88. Accordingly, the trephine 12 can be very versatile and convenient for use.

In summary, the system 10 and methods described above can allow for several advantages. For instance, only one incision may be necessary for completing the operation because the trephine 12 is flexible and can be routed more easily within the patient. Also, the trephine 12 can be routed around anatomical structures very conveniently. Thus, the procedure can cause the patient less trauma, and the system 10 can provide substantial versatility for use in a wide variety of patients and procedures.

While the donor site 62 and the defect site 68 are located in the same joint in the method described above, it will be appreciated that the donor site 62 and defect site 68 can be located in separate areas of the body. Moreover, while the method described above includes both harvesting cartilage and placing the harvested cartilage on a defect site 68, it will be appreciated that the system 10 can be used only to harvest cartilage or only to place cartilage on a defect site 68 without departing from the scope of the present disclosure. In addition, the system 10 can be used to place any suitable material on the defect site 68 (including anatomical cartilage from the same patient, anatomical cartilage from another patient, anatomical cartilage from another species, or artificial cartilage) without departing from the scope of the present disclosure.

Moreover, the foregoing discussion discloses and describes merely exemplary embodiments of the present disclosure. One skilled in the art will readily recognize from such discussion, and from the accompanying drawings and claims, that various changes, modifications and variations may be made therein without departing from the spirit and scope of the disclosure as defined in the following claims. For instance, the sequence of the blocks of the method described herein can be changed without departing from the scope of the present disclosure.

What is claimed is:

1. A system for repairing cartilage comprising:
    a flexible trephine having a passage extending along a longitudinal axis of the trephine, a distal end, and a proximal end, the distal end including a cutting member operable to cut a cartilage plug from a donor site, the passage operable to receive the cartilage plug, the trephine being flexible to selectively move between a first position at the donor site in which the longitudinal axis is substantially linear and a second position at an implant site in which the longitudinal axis is nonlinear;
    a first guide tool that is removably coupled to the trephine, the first guide tool operable to selectively move a distal end of the trephine between the first and second positions;
    a second guide tool including a rigid cannulated tube with a non-linear longitudinal axis, the trephine capable of being removably received within the tube to guide the trephine along the non-linear longitudinal axis as the distal end of the trephine advances in the tube from the first position to the second position; and
    an ejector tool that ejects the cartilage plug from the passage toward a defect site.

2. The system of claim 1, wherein the trephine is made of a rigid material, and wherein the trephine includes at least one slot, the trephine flexing about the slot as the trephine moves from the first position to the second position.

3. The system of claim 1, wherein the ejector tool includes an elongate, flexible rod that is removably received in the passage.

4. The system of claim 1, wherein the first guide tool includes a coupling portion that operably couples to the trephine and an elongate handle that extends from the coupling portion.

5. The system of claim 4, wherein the coupling portion is resilient so as to resiliently receive the trephine and to removably couple to the trephine.

6. The system of claim 4, wherein the coupling portion is substantially C-shaped with an opening, the trephine movable through the opening to flex the coupling portion.

7. A system for repairing cartilage, comprising:
a flexible trephine extending along a longitudinal axis between a distal end and a proximal end, the distal end including a cutting member operable to cut a tissue plug from a donor site and the trephine including a passage operable to receive the tissue plug, the trephine being flexible to selectively move between a first position at the donor site in which the longitudinal axis is substantially linear and a second position at an implant site in which the longitudinal axis is nonlinear;
a first guide tool configured to be removably coupled to the trephine, the first guide tool operable to selectively move a distal end of the trephine between the first position and the second position;
a second guide tool including a rigid cannulated tube with a non-linear longitudinal axis, the trephine capable of being removably received within the tube to guide the trephine along the non-linear longitudinal axis as the distal end of the trephine advances in the tube from the first position to the second position; and
an ejector tool configured to cooperate with the trephine to eject the tissue plug from the passage.

8. The system of claim 7, wherein a first end of the second guide tool is configured to be placed near a tissue receiving site and the trephine is configured to be moved through the cannulated tube from a second end along a non-linear longitudinal axis within the rigid cannulated tube.

9. The system of claim 7, wherein the cannulated tube is selectively bendable to selectively vary the longitudinal axis of the cannulated tube.

10. The system of claim 7, wherein the first guide tool includes a coupling portion to removably couple near at least the distal end of the trephine to move the trephine between the first position and the second position.

11. The system of claim 10, wherein the coupling portion is substantially C-shaped with an opening, the trephine movable through the opening to flex the coupling portion.

12. The system of claim 10, wherein the coupling portion engages substantially only near the distal end of the trephine.

13. The system of claim 7, wherein the trephine is formed of a rigid material and includes at least one slot, the trephine is configured to flex relative to the slot as the trephine moves from the first position to the second position.

14. The system of claim 13, wherein the slot includes at least a portion that is continuously extending helically about the longitudinal axis of the trephine.

15. The system of claim 7, wherein the ejector tool includes an elongate, flexible rod that is removably received in the passage.

16. A system for repairing cartilage, comprising:
a trephine having a flexible exterior wall extending along a first longitudinal axis between a proximal end to a distal end and having a passage therethrough, wherein the trephine is operable to be moved from a first position at a donor site in which the first longitudinal axis is substantially linear and to a second position at an implant site in which the first longitudinal axis is nonlinear;
a first guide tool configured to be removably coupled to the trephine, the second guide tool operable to selectively move the distal end of the trephine between the first position and the second position; and
a second guide tool configured to operably engage at least a portion of the flexible exterior wall to move the trephine from the first position to the second position, wherein the first guide tool is a rigid cannulated tube including a first portion having a linear longitudinal axis and a second portion having a non-linear longitudinal axis, the trephine capable of being removably received within the tube to guide the trephine along the non-linear longitudinal axis as the distal end of the trephine advances in the tube from the first position to the second position.

17. The system of claim 16, wherein the flexible exterior wall is formed of a rigid material having at least one slot formed therethrough to allow a first portion of the flexible exterior wall to move relative to the second portion of the flexible exterior wall.

18. The system of claim 16, wherein the trephine is configured to pass through the cannulated tube to move from the first position to the second position.

19. The system of claim 18, wherein the cannulated tube includes a passage to receive the trephine and the trephine can flex and bend along a curvature of the cannulated tube as the respective trephine advances along the cannulated tube.

20. The system of claim 16, further comprising:
an ejector portion configured to assist in removing a tissue portion from the passage.

\* \* \* \* \*